US010107716B2

(12) United States Patent
Ascencio et al.

(10) Patent No.: US 10,107,716 B2
(45) Date of Patent: Oct. 23, 2018

(54) SYSTEMS AND METHODS FOR TESTING A GAS TURBINE

(71) Applicant: General Electric Company, Schenectady, NY (US)

(72) Inventors: Vasanthi Ascencio, Atlanta, GA (US); Sanjeev Shyam Heda, Atlanta, GA (US); Dibakar Chandra, Atlanta, GA (US); Ricardo Emilio Magana, Nuevo León (MX); Bryan Li, Schenectady, NY (US); Benjamin Moises Morales, Nuevo León (MX); Jorge Cano, Querétaro (MX)

(73) Assignee: General Electric Company, Schenectady, NY (US)

( * ) Notice: Subject to any disclaimer, the term of this patent is extended or adjusted under 35 U.S.C. 154(b) by 349 days.

(21) Appl. No.: 14/827,776

(22) Filed: Aug. 17, 2015

(65) Prior Publication Data

US 2017/0052092 A1    Feb. 23, 2017

(51) Int. Cl.
*G01N 33/00* (2006.01)
*G01M 15/14* (2006.01)
(Continued)

(52) U.S. Cl.
CPC .............. *G01M 15/14* (2013.01); *F02C 9/28* (2013.01); *G01N 30/02* (2013.01); *G01N 33/0006* (2013.01); *G01N 2030/025* (2013.01)

(58) Field of Classification Search
CPC .................................................. G01N 33/0006
See application file for complete search history.

(56) References Cited

U.S. PATENT DOCUMENTS 5,600,893 A    2/1997 Phillips
6,529,849 B2    3/2003 Umezawa et al.
(Continued)

FOREIGN PATENT DOCUMENTS

EP    2450551 A2    5/2012
GB    2074324 A    10/1981

OTHER PUBLICATIONS

European Search Report and Opinion issued in connection with corresponding European Application No. 16184152.3 dated Feb. 3, 2017.

*Primary Examiner* — Robert R Raevis
(74) *Attorney, Agent, or Firm* — Eversheds-Sutherland (US) LLP (57) ABSTRACT

Embodiments of the disclosure relate to performance testing of a gas turbine. In one embodiment, a gas turbine performance testing system can include a server, a transducer system, a signal converter, and an automated gas chromatograph. The transducer system acquires one or more functional parameters of the gas turbine and the signal converter converts the functional parameters acquired by the transducer system to gas turbine operational data. The automated gas chromatograph automatically analyzes a test sample of a natural gas that is used to operate the gas turbine. The gas turbine operational data generated by the signal converter and the analysis information obtained from the test sample are provided to the server for propagating via a communication network, to a client computer where the gas turbine operational data and the analysis information can be used to obtain a gas turbine performance test result.

20 Claims, 4 Drawing Sheets

(51) Int. Cl.
    *G01N 30/02*     (2006.01)
    *F02C 9/28*     (2006.01)

(56) References Cited

U.S. PATENT DOCUMENTS

| | | |
|---|---|---|
| 7,065,471 B2 | 6/2006 | Gotoh et al. |
| 7,143,009 B2 | 11/2006 | Patanian |
| 7,243,042 B2 | 7/2007 | Plotts et al. |
| 7,840,332 B2 | 11/2010 | Saravanapriyan et al. |
| 2006/0174630 A1 | 8/2006 | Hellat et al. |
| 2007/0203669 A1 | 8/2007 | Hayashi |
| 2010/0162678 A1* | 7/2010 | Annigeri .................. F02C 3/20 60/39.281 |

* cited by examiner

SYSTEMS AND METHODS FOR TESTING A GAS TURBINE

This disclosure relates to gas turbines, and more particularly, to systems and methods for testing a gas turbine.

BACKGROUND OF THE DISCLOSURE

Typically, a gas turbine is a complex piece of machinery that includes a large number of stationary as well as moving parts that come into play when the gas turbine is placed in an operating condition. As can be expected, these various parts may deteriorate or fail over time and may need to be replaced when the overall performance of the gas turbine suffers as a result of a deteriorated or failed part. However, it is generally undesirable to wait for a part to malfunction or to fail completely before replacing the failed part, especially if such a replacement necessitates shutting down the gas turbine. Consequently, in order to avoid such a situation, a gas turbine may be subjected to periodic testing in order to assess various components of the gas turbine and to ensure that the gas turbine is operating at a satisfactory level of performance.

In some cases, the periodic performance testing may be carried out by a manufacturer of the gas turbine (or by a selling entity of the gas turbine) as a part of a warranty agreement or a service contract agreement. Typically such testing is carried out on-site at a customer location after the customer has made suitable arrangements for having the gas turbine tested. Understandably, given the complexity of the gas turbine and the various operating conditions that the gas turbine may be subjected to, the on-site periodic testing can be a complex and elaborate procedure involving a significant amount of time and money on the part of the customer as well as on the part of the manufacturer or selling entity.

BRIEF DESCRIPTION OF THE DISCLOSURE

Embodiments of the disclosure are generally directed to systems and methods for performance testing of a gas turbine. According to one example embodiment of the disclosure, a gas turbine performance testing system can include a server, a transducer system, a signal converter, and an automated gas chromatograph. The server is communicatively coupled to a client computer via a communication network. The transducer system is configured to acquire one or more functional parameters of a gas turbine. The signal converter, which is communicatively coupled to the transducer system, is configured to convert the acquired functional parameters into gas turbine operational data that is provided to the server for propagating to the client computer. The automated gas chromatograph, which is also communicatively coupled to the server, is configured to automatically analyze a test sample of a natural gas that is used to operate the gas turbine and to provide analysis information obtained from the test sample to the server for propagating to the client computer for combining with the gas turbine operational data to obtain a gas turbine performance test result.

According to another example embodiment of the disclosure, a method of executing a performance test upon a gas turbine includes using a transducer system to acquire one or more functional parameters of the gas turbine. A signal converter is used to convert the acquired functional parameters into gas turbine operational data, which is provided to a server. The method further includes using an automated gas chromatograph to automatically analyze a test sample of a natural gas that is used to operate the gas turbine, and transferring from the automated gas chromatograph to the server, analysis information associated with the test sample of the natural gas. The server transmits the gas turbine operational data and the analysis information obtained from the test sample of the natural gas to a client computer, via a communication network, for processing in the client computer to obtain a performance test result based on the gas turbine operational data and/or the analysis information obtained from the test sample of the natural gas.

According to yet another example embodiment of the disclosure, a computer-readable storage medium can be provided. The computer-readable storage medium has stored thereon, instructions executable by a computer for performing operations that can include acquiring via a transducer system, one or more operating parameters of a gas turbine; converting via a signal converter, the acquired operating parameters to gas turbine operational data; automatically analyzing via a automated gas chromatograph, a test sample of a natural gas that is used to operate the gas turbine; and transmitting the gas turbine operational data and analysis information obtained from the test sample of the natural gas, via a communication network, for processing in a client computer to obtain a gas turbine performance test result.

Other embodiments and aspects of the disclosure will become apparent from the following description taken in conjunction with the following drawings.

BRIEF DESCRIPTION OF THE DRAWINGS

Having thus described the disclosure in general terms, reference will now be made to the accompanying drawings, which are not necessarily drawn to scale, and wherein:

DETAILED DESCRIPTION OF THE DISCLOSURE

The disclosure now will be described more fully hereinafter with reference to the accompanying drawings, in which example embodiments of the disclosure are shown. This disclosure may, however, be embodied in many different forms and should not be construed as limited to the example embodiments set forth herein; rather, these embodiments are provided so that this disclosure will satisfy applicable legal requirements. Like numbers refer to like elements throughout.

In terms of a general overview, certain embodiments of the systems and methods described herein are directed to carrying out performance testing of a gas turbine. In some example implementations, performance testing may be used to evaluate a gas turbine that is operating at a distant location, in order to identify various potential hardware and/or software issues that may adversely affect the performance of the gas turbine either currently and/or in the future. In some other example implementations, the performance testing can be a pre-test procedure that can be conducted from a remote off-site location prior to execution of an on-site test that involves test personnel visiting a location where the gas turbine is located and carrying out a full-fledged on-site performance test of the gas turbine. Performing the remote pre-test prior to execution of an on-site test can provide various benefits such as, for example, allowing a customer to pre-emptively address any issues that may adversely impact the on-site test; assisting the manufacturer or selling entity to provide advice or recommendations to the customer in order reduce an amount of time and money spent on the on-site test; and collecting test data ahead of time to avoid incurring certain monetary costs. These monetary costs may include for example, costs associated with test personnel spending time on-site collecting certain types of test data that can be collected ahead of time at an off-site test facility, or costs associated with certain computations that can be done ahead of time so as to avoid on-site wait times or delays.

Figure 1:
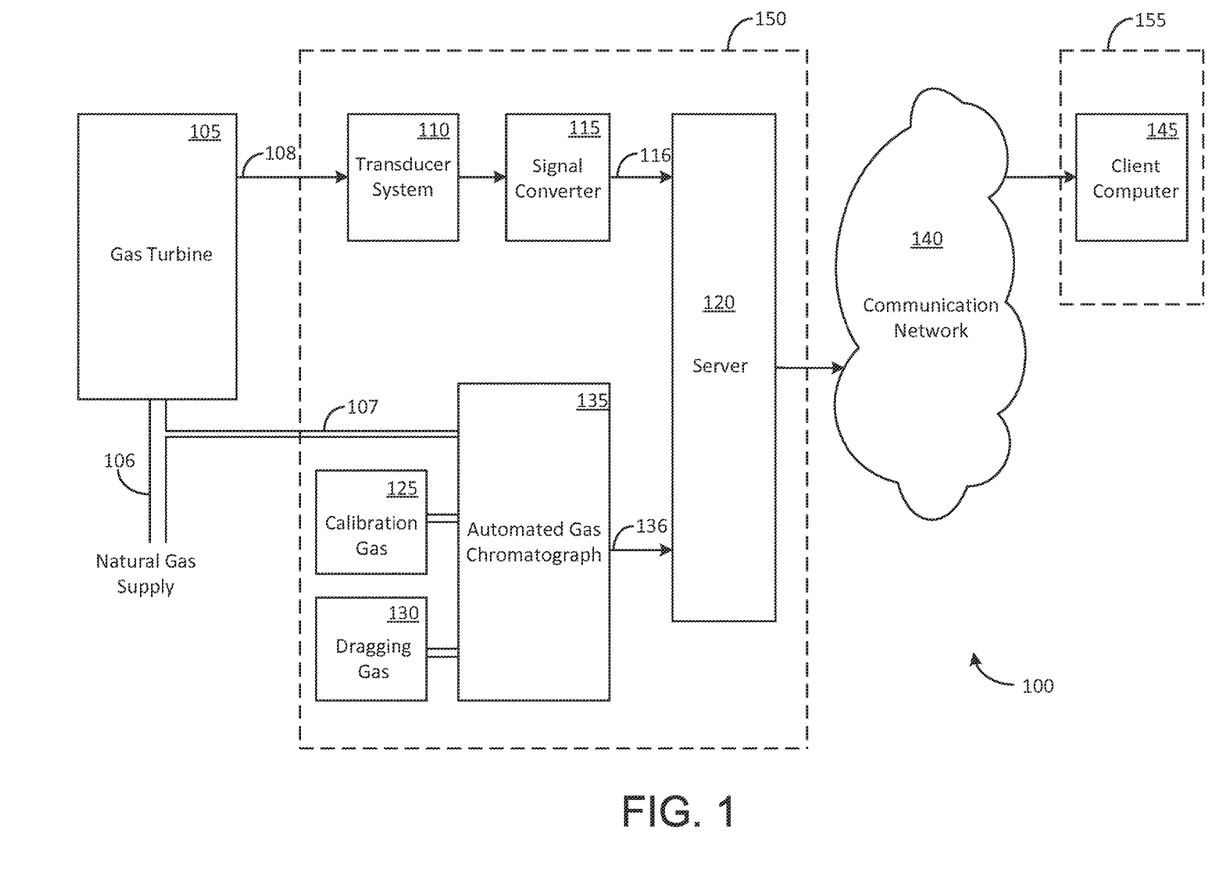
FIG. 1 illustrates an example performance testing system for remote testing of a gas turbine in accordance with certain embodiments of the disclosure.

Attention is drawn to FIG. 1, which illustrates an example performance testing system 100 for remote testing of a gas turbine 105 in accordance with certain embodiments of the disclosure. The performance testing system 100 can be broadly partitioned into two segments. The first segment, which is identified by a dashed box 150, can be referred to as a remote segment and the second segment, which is identified by a dashed box 155, can be referred to as a local segment from which a remote performance test can be carried out upon the gas turbine 105 via a communications network 140, by using a client computer 145 in accordance with the disclosure. As such, this arrangement can be interpreted as a performance testing system 100 that uses a "local" element (in the form of the exemplary client computer 145) to interact, via the communication network 140, with various "remote" elements (some examples of which are shown in the remote segment 150) for executing a remote performance test upon the gas turbine 105. Solely for convenience of description, the various elements shown in the remote segment 150 may be referred to henceforth as "remote" elements. However, it should be understood that in accordance with the disclosure, it is not a requirement that all "remote" elements be co-located at a single location. In some exemplary embodiments, two or more of the remote elements shown in the remote segment 150 can be physically placed at different locations.

The client computer 145 is communicatively coupled to a remote server 120 via the communication network 140, which can be any of one or more networks such as, for example, a corporate wide area network or a public wide area network (e.g., the Internet). The remote server 120 that is shown in FIG. 1 is a pictorial representation of one or more computing elements and can include for example, multiple servers communicatively coupled to each other via another network (not shown) or via the communication network 140. These multiple servers can include for example, a sequential query language (SQL) server, a historian server, and a service-oriented architecture (SOA) server.

The gas turbine 105 typically incorporates various parts (not shown) such as a compressor that provides pressurized air to a combustor. In the combustor, the pressurized air is mixed with fuel and the mixture ignited to produce hot combustion gases. These hot combustion gases flow downstream to one or more turbine rotors that extract energy from the hot combustion gases for powering the compressor and providing a rotational output that can be used for a variety of tasks, such as, for example generating electric power from an electric generator or for providing thrust to an aircraft. The fuel that is provided to the gas turbine 105, which may be referred to herein as natural gas, is conveyed to the gas turbine 105 via a gas supply line 106. A portion of the natural gas transported on the gas supply line 106 is diverted via an auxiliary gas line 107 to a remote automated gas chromatograph 135 that can automatically analyze a test sample of the natural gas as a part of a remote performance test of the gas turbine 105 in accordance with the disclosure. The automatic analysis of the test sample can be used to obtain fuel-related information such as, for example, a composition of the natural gas in accordance with a standard that is known in the industry as ASTM 1945. In one example implementation, a natural gas sample can be tested for identifying C6+ hexane composition. Thus, analysis information can include fuel-related information, such as a particular fuel composition.

A calibration gas container 125 can be used to supply calibration gas to the remote automated gas chromatograph 135 as a part of the remote performance test of the gas turbine 105 in accordance with the disclosure. The calibration gas may be provided to the remote automated gas chromatograph 135 for calibrating the remote automated gas chromatograph 135 prior to providing a sample of the natural gas via the gas supply line 106 for carrying out the remote performance test. The remote automated gas chromatograph 135 can be also provided with what is referred to herein as a "dragging" gas, from a dragging gas container 130. The dragging gas can be used in some example implementations for pushing the natural gas sample through the remote automated gas chromatograph 135 during execution of the remote performance test and can also be used in some example implementations for flushing the remote automated gas chromatograph 135 after the natural gas sample has been automatically analyzed in the remote automated gas chromatograph 135. The dragging gas can be an inert gas that does not affect performance test results obtained from analyzing the natural gas sample drawn from the gas supply line 106 via the auxiliary gas line 107.

The gas chromatography test results provided by the automated gas chromatograph 135 can constitute one part of a cumulative performance test result obtained by performing a remote performance test upon the gas turbine 105 in accordance with the disclosure. Another part of the cumulative performance test result can be derived by using a remote transducer system 110 that is communicatively coupled to the gas turbine 105. The transducer system 110 can include one or more of a variety of transducers such as for example, pressure transducers and temperature sensors that can be used for obtaining measurements of various functional parameters of the gas turbine 105. Some example functional parameters of the gas turbine 105 can include an operating static pressure, an operating temperature, and/or an operating differential pressure associated with one or more components of the gas turbine 105.

In one example implementation, the transducer system 110 is configured to automatically obtain such measurements in real time. The real time measurements can be used for carrying out a remote performance test of the gas turbine 105 in real time. In another example implementation, the transducer system 110 is configured to automatically obtain measurements on a periodic basis such as for example, on an hourly basis, a daily basis, a weekly basis or a monthly basis. The measurements can be used in the form of historical data when executing a real time, a near-real time, or a non-real time remote performance test of the gas turbine 105.

In one example implementation, the transducer system 105 is configured to automatically obtain such measurements in real time. The real time measurements can be used for carrying out a remote performance test of the gas turbine 105 in real time. In another example implementation, the transducer system 105 is configured to automatically obtain measurements on a periodic basis such as, for example, on an hourly basis, a daily basis, a weekly basis or a monthly basis. The measurements can be used in the form of historical data when executing a real time, a near-real time, or a non-real time remote performance test of the gas turbine 105.

The measured functional parameters of the gas turbine 105 are coupled from the remote transducer system 110 into a remote signal converter 115. The remote signal converter 115 conditions the measured functional parameters into a standardized format and provides gas turbine operational data in the standardized format to the remote server 120. Thus, operational data can include, for example, real time measurements of static pressures, operating temperatures, and operating differential pressure associated with one or more components of the gas turbine 105. The combination of the remote transducer system 110, the remote signal converter 115 and the remote server 120 allows for executing a fully automated measurement procedure that can be performed without manual intervention by personnel on-site where the gas turbine 105 is located.

The remote server 120 transmits the gas turbine operational data obtained from the 115 and the gas chromatography test results obtained from the remote automated gas chromatograph 135 either in raw form or in a processed format (after performing some data processing in the remote server 120), to the client computer 145 via the communication network 140. The client computer 145 as shown in FIG. 1 is a pictorial representation of one or more computing devices such as a laptop computer, a desktop computer, a tablet, or a smartphone, and can include multiple client computers communicatively coupled to each other via another network (not shown) or the communications network 120. The client computer 145 can use the gas turbine operational data and the gas chromatography test results received from the remote server 120 to calculate various performance metrics of the gas turbine 105 such as, for example, thermal metrics and fuel related metrics. The thermal metrics of the gas turbine 105 may be calculated for example by applying a heat rate calculation method that is compliant with ASME PTC-22 test code. Furthermore, the client computer 145 can use the gas turbine performance test result and the gas chromatography test results received from the remote server 120 to calculate other performance metrics such as, for example, a heat-related performance metric, a pressure-related performance metric, a fuel-related performance metric, or a combination of two or more of the heat-related performance metric, the pressure-related performance metric, and the fuel-related performance metric.

Figure 2:
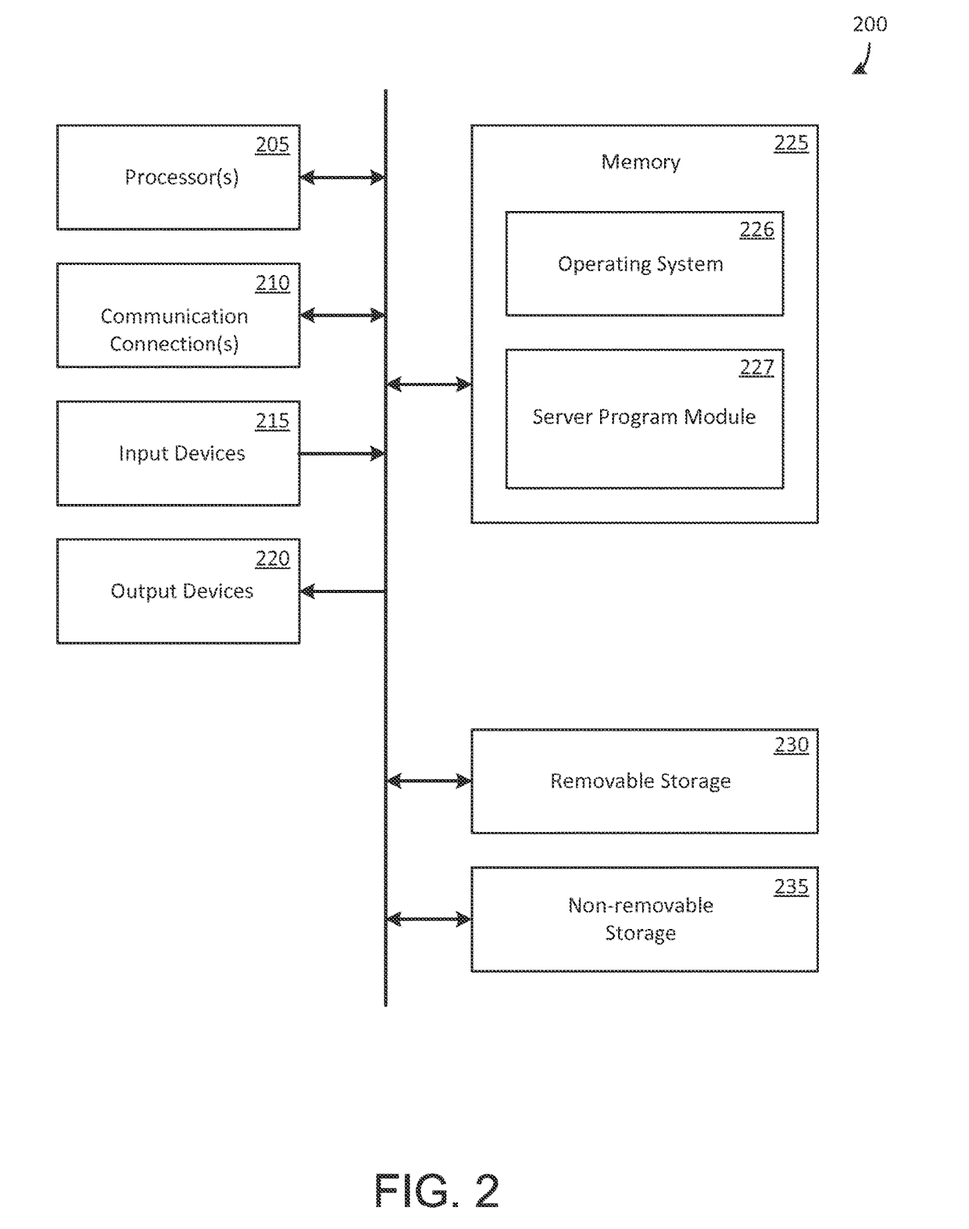
FIG. 2 illustrates an example server computer configured for remote performance testing of a gas turbine in accordance with certain embodiments of the disclosure.

Attention is now drawn to FIG. 2, which illustrates an example remote server 200 configured for remote performance testing of the gas turbine 105 in accordance with certain embodiments of the disclosure. The remote server 200, which represents a computer system that can be used for executing the functionality of the remote server 120 shown in FIG. 1, incorporates a processor 205 for executing certain operational aspects associated with a remote performance test of a gas turbine in accordance with certain embodiments of the disclosure. The processor 205 is capable of communicating with a memory 225. The processor 205 can be implemented and operated using appropriate hardware, software, firmware, or combinations thereof. Software or firmware implementations can include computer-executable or machine-executable instructions written in any suitable programming language to perform the various functions described. In one embodiment, instructions associated with a function block language can be stored in the memory 225 and executed by the processor 205.

The memory 225 can be used to store program instructions that are loadable and executable by the processor 205, as well as to store data generated during the execution of these programs. Depending on the configuration and type of the computer 200, the memory 225 can be volatile (such as random access memory (RAM)) and/or non-volatile (such as read-only memory (ROM), flash memory, etc.). In some embodiments, the memory devices can also include additional removable storage 230 and/or non-removable storage 235 including, but not limited to, magnetic storage, optical disks, and/or tape storage. The disk drives and their associated computer-readable media can provide non-volatile storage of computer-readable instructions, data structures, program modules, and other data for the devices. In some implementations, the memory 225 can include multiple different types of memory, such as static random access memory (SRAM), dynamic random access memory (DRAM), or ROM.

The memory 225, the removable storage 230, and the non-removable storage 235 are all examples of computer-readable storage media. For example, computer-readable storage media can include volatile and non-volatile, removable and non-removable media implemented in any method or technology for storage of information such as computer-readable instructions, data structures, program modules or other data. Additional types of computer storage media that can be present include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile discs (DVD) or other optical storage, magnetic cassettes, magnetic tapes, magnetic disk storage or other magnetic storage devices, or any other medium which can be used to store the desired information and which can be accessed by the devices. Combinations of any of the above should also be included within the scope of computer-readable media.

Computer 200 can also include one or more communication connections 210 that can allow a control device (not shown) to communicate with devices or equipment capable of communicating with the computer 200. The connections can be established via various data communication channels or ports, such as USB or COM ports to receive cables connecting the control device to various other devices on a network. In one embodiment, the control device can include Ethernet drivers that enable the control device to communicate with other devices on the network. According to various embodiments, communication connections 210 can be established via a wired and/or wireless connection on the network.

The computer 200 can also include one or more input devices 215, such as a keyboard, mouse, pen, voice input device, and touch input device. It can further include one or more output devices 220, such as a display, printer, and speakers.

In other embodiments, however, computer-readable communication media can include computer-readable instructions, program modules, or other data transmitted within a data signal, such as a carrier wave, or other transmission. As used herein, however, computer-readable storage media do not include computer-readable communication media.

Turning to the contents of the memory 225, the memory 225 can include, but is not limited to, an operating system (OS) 226 and one or more application programs or services for implementing the features and aspects disclosed herein. Such applications or services can include a server program module 227 for executing a remote portion of a performance test of a gas turbine. In one embodiment, the server program module 227 can be implemented by software that is provided in configurable control block language and is stored in non-volatile memory. When executed by the processor 205, the server program module 227 implements the various functionalities and features associated with the remote server 120 described in this disclosure.

Figure 3:
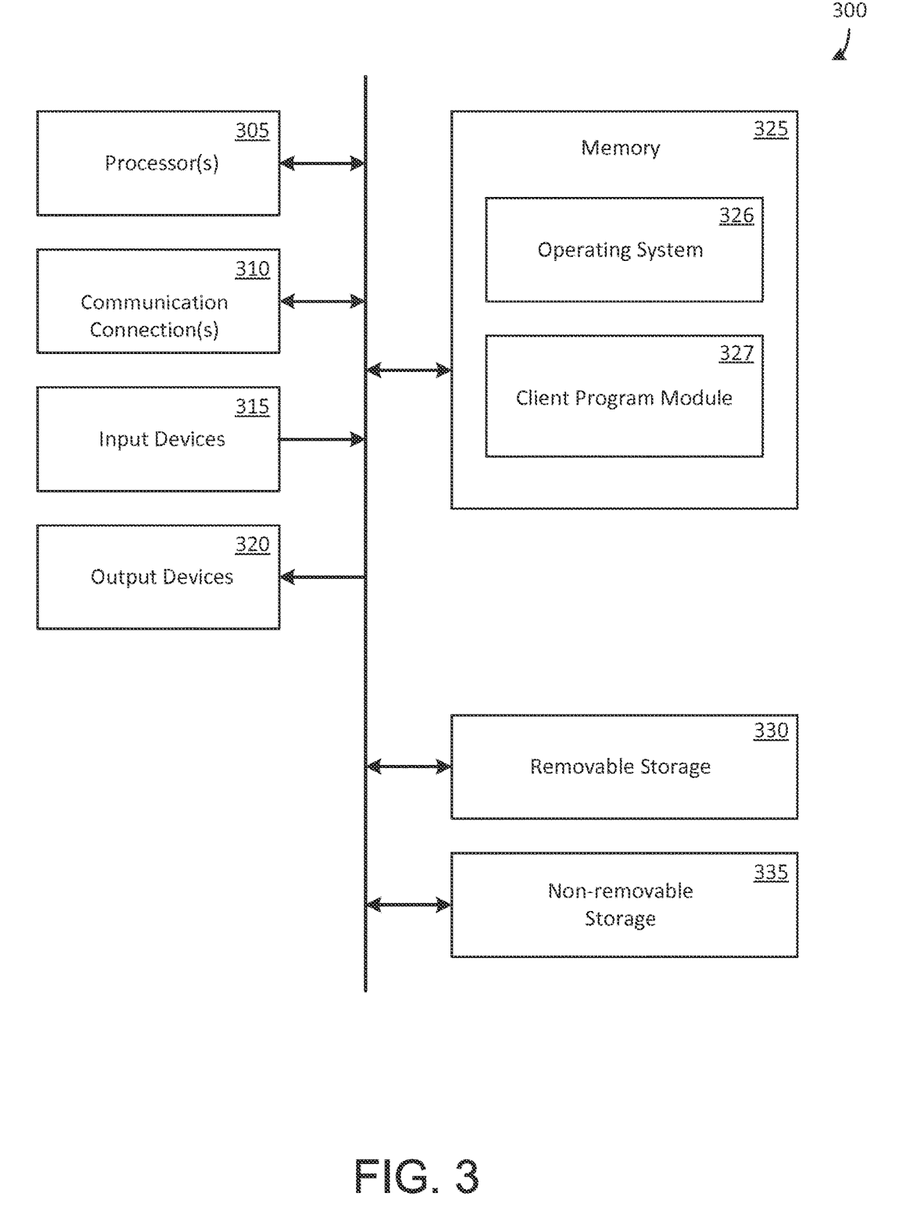
FIG. 3 illustrates an example client computer configured for remote performance testing of a gas turbine in accordance with certain embodiments of the disclosure.

FIG. 3 illustrates an example client computer 300 configured for remote performance testing of the gas turbine 105 in accordance with certain embodiments of the disclosure. The client computer 300, which represents a computer system that can be used for executing the functionality of the client computer 145 shown in FIG. 1, incorporates a processor 305 and other elements for executing certain operational aspects associated with a remote performance test of a gas turbine in accordance with certain embodiments of the disclosure. The features of the processor 305 as well as those of the other elements of the client computer 300 can be understood in view of the description of similar elements that is provided above with respect to the remote server 200 and will not be repeated here in the interest of brevity. These various elements are adapted for implementing the client side operations of a remote performance test of a gas turbine in accordance with certain embodiments of the disclosure. Accordingly, attention is drawn to the memory 325, which can include, but is not limited to, an operating system (OS) 326 and one or more application programs or services for implementing the features and aspects disclosed herein. Such applications or services can include a client program module 327 for executing a local client-side portion of a remote performance test of a gas turbine. In one embodiment, the client program module 327 can be implemented by software that is provided in configurable control block language and is stored in non-volatile memory. When executed by the processor 305, the client program module 327 implements the various functionalities and features associated with the client computer 145 described in this disclosure.

Figure 4:
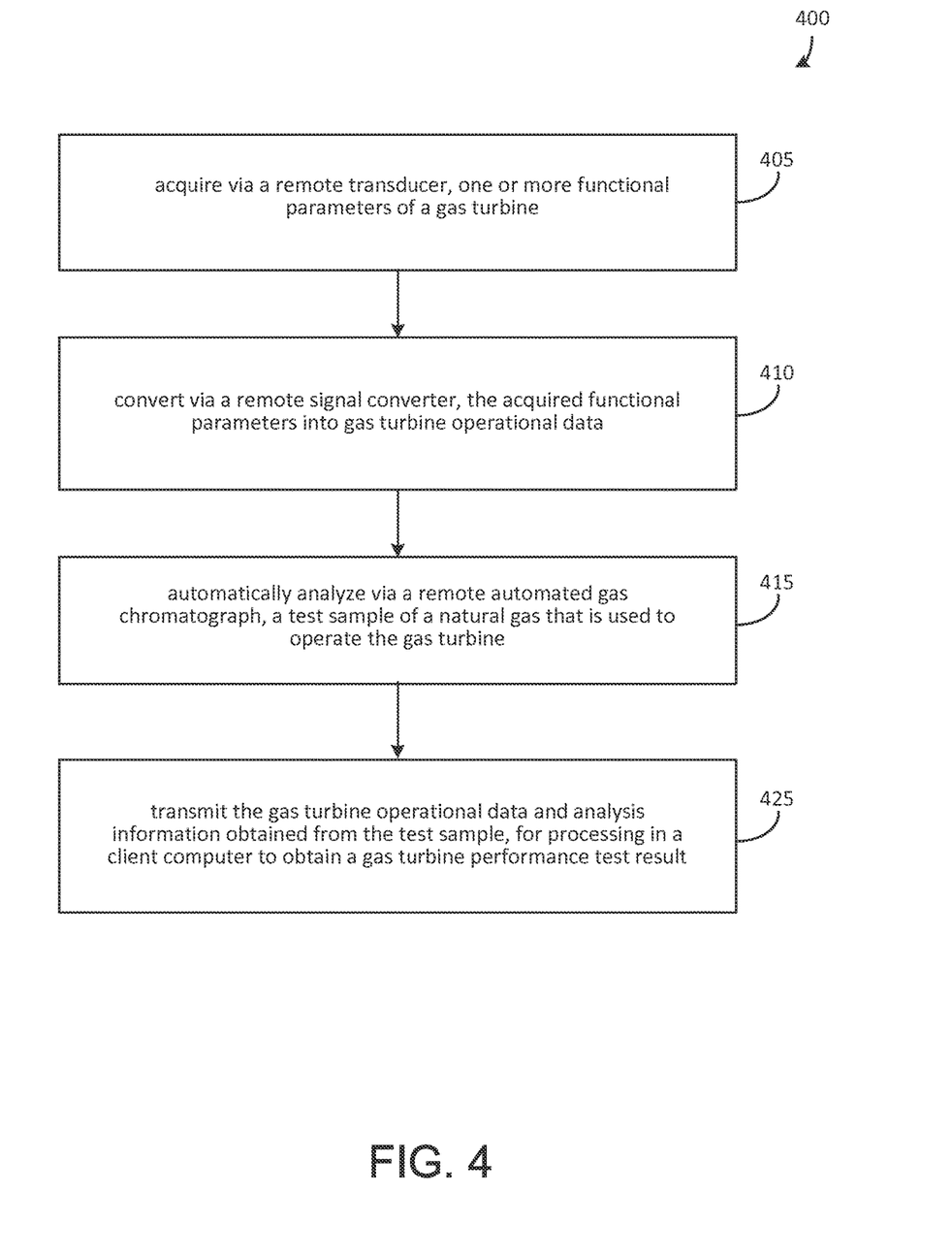
FIG. 4 illustrates an example flowchart of a method for remote performance testing of a gas turbine in accordance with certain embodiments of the disclosure.

FIG. 4 illustrates an example flowchart 400 of a method for remote performance testing of a gas turbine according to at least one embodiment of the disclosure. The flowchart 400 represents a series of operations that can be executed by the interaction of the various functional blocks shown in FIG. 1, and particularly by the remote elements of the performance testing system 100 shown in FIG. 1. More particularly, the flowchart 400 includes a block 405 representing an operation that can be executed by the server 120 via the remote transducer system 110 and the remote signal converter 115. Specifically, in the block 405, one or more functional parameters of a gas turbine are acquired via a remote transducer, such as, for example the remote transducer system 110. In block 410, the acquired functional parameters are converted into gas turbine operational data by a remote signal converter such as, for example, the remote signal converter 115. In block 415, a test sample of a natural gas that is used to operate the gas turbine is automatically analyzed by a remote automated gas chromatograph such as, for example, the remote automated gas chromatograph 135. In block 425, the gas turbine operational data derived from the acquired functional parameters of the gas turbine and the analysis information derived from the remote automated gas chromatograph are transmitted to a client computer, such as, for example, the client computer 145, for processing to obtain a gas turbine performance test result.

References are made herein to block diagrams of systems, methods, and computer program products according to example embodiments of the disclosure. It will be understood that at least some of the blocks of the block diagrams, and combinations of blocks in the block diagrams, respectively, can be implemented at least partially by computer program instructions. These computer program instructions can be loaded onto a general purpose computer, special purpose computer, special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions can also be stored in a computer-readable memory that can direct a computer or other programmable data processing apparatus to function in a particular manner, such that the instructions stored in the computer-readable memory produce an article of manufacture including instruction means that implement the function specified in the block or blocks. The computer program instructions can also be loaded onto a computer or other programmable data processing apparatus to cause a series of operational elements to be performed on the computer or other programmable apparatus to produce a computer implemented process such that the instructions that execute on the computer or other programmable apparatus provide elements for implementing the functions specified in the block or blocks.

One or more components of the systems and one or more elements of the methods described herein can be implemented through an application program running on an operating system of a computer. They also can be practiced with other computer system configurations, including handheld devices, multiprocessor systems, microprocessor based, or programmable consumer electronics, mini-computers, mainframe computers, etc.

Application programs that are components of the systems and methods described herein can include routines, programs, components, data structures, etc. that implement certain abstract data types and perform certain tasks or actions. In a distributed computing environment, the application program (in whole or in part) can be located in local memory, or in other storage. In addition, or in the alternative, the application program (in whole or in part) can be located in remote memory or in storage to allow for circumstances where tasks are performed by remote processing devices linked through a communications network.

Many modifications and other embodiments of the example descriptions set forth herein to which these descriptions pertain will come to mind having the benefit of the teachings presented in the foregoing descriptions and the associated drawings. Thus, it will be appreciated the disclosure may be embodied in many forms and should not be limited to the example embodiments described above. Therefore, it is to be understood that the disclosure is not to be limited to the specific embodiments disclosed and that modifications and other embodiments are intended to be included within the scope of the appended claims. Although That which is claimed is:

1. A gas turbine performance testing system comprising:
a server communicatively coupled to a client computer via a communication network;
a transducer system configured to acquire one or more functional parameters of a gas turbine;
a signal converter communicatively coupled to the transducer system, the signal converter configured to convert the acquired one or more functional parameters into gas turbine operational data that is provided to the server for propagating to the client computer; and
an automated gas chromatograph communicatively coupled to the server, wherein the automated gas chromatograph is coupled to a gas supply line of the gas turbine and is configured to automatically obtain a test sample from the gas supply line, and wherein a calibration gas container and a dragging gas container are each coupled to the automated gas chromatograph, the dragging gas to provide an inert gas for moving the test sample to the automated gas chromatograph, the automated gas chromatograph further configured to automatically analyze the test sample used to operate the gas turbine and to provide a gas chromatography test result to the server for propagating to the client computer, the client computer configured to derive gas turbine performance test results comprising the gas chromatography test result and the gas turbine operational data, wherein at least one of the gas turbine performance test results further comprise at least one of: a heat-related performance metric, a pressure-related performance metric, or a fuel-related performance metric.

2. The system of claim 1, wherein the transducer system is configured to acquire the one or more functional parameters of the gas turbine in one of a real-time mode of operation or a periodic mode of operation.

3. The system of claim 1, wherein the one or more functional parameters comprises at least one of an operating static pressure, an operating temperature, or an operating differential pressure.

4. The system of claim 1, wherein the automated gas chromatograph is coupled to a gas supply line of the gas turbine and is configured to automatically obtain the test sample from the gas supply line.

5. The system of claim 4, further comprising:
a calibration gas container coupled to the automated gas chromatograph to provide calibration gas for calibrating the automated gas chromatograph; and
a dragging gas container coupled to the automated gas chromatograph to provide dragging gas for pushing the test sample of the natural gas through the automated gas chromatograph.

6. The system of claim 5, wherein the dragging gas is an inert gas.

7. The system of claim 1, wherein the gas turbine performance test results further comprise at least one of a heat-related performance metric, a pressure-related performance metric, or a fuel-related performance metric.

8. A method of executing a performance test upon a gas turbine, the method comprising:
using a transducer system to acquire one or more functional parameters of the gas turbine;
using a signal converter to convert the acquired one or more functional parameters into gas turbine operational data;
providing the gas turbine operational data to a server;
obtaining a gas chromatography test result by using an automated gas chromatograph to automatically analyze a test sample of a natural gas that is used to operate the gas turbine, wherein the automated gas chromatograph is coupled to a gas supply line of the gas turbine and is configured to automatically obtain a test sample from the gas supply line, and wherein a calibration gas container and a dragging gas container are each coupled to the automated gas chromatograph, the dragging gas to provide an inert gas for moving the test sample to the automated gas chromatograph;
transferring from the automated gas chromatograph to the server, the gas chromatography test result; and
transmitting from the server to a client computer, via a communications network, the gas turbine operational data and the gas chromatography test result, for processing in the client computer to obtain gas turbine performance test results based on the gas turbine operational data and the gas chromatography test result, wherein at least one of the gas turbine performance test results further comprise at least one of: a heat-related performance metric, a pressure-related performance metric, or a fuel-related performance metric.

9. The method of claim 8, wherein the one or more functional parameters of the gas turbine is acquired in one of a real-time mode of operation or a periodic mode of operation.

10. The method of claim 8, wherein the one or more functional parameters comprises at least one of an operating static pressure, an operating temperature, or an operating differential pressure.

11. The method of claim 8, wherein the automated gas chromatograph is coupled to a gas supply line of the gas turbine and automatically obtains the test sample of the natural gas from the gas supply line.

12. The method of claim 11, further comprising:
using a calibration gas container to provide to the automated gas chromatograph calibrating gas for calibrating the automated gas chromatograph; and
using a dragging gas container to provide to the automated gas chromatograph dragging gas for pushing the test sample of the natural gas through the automated gas chromatograph.

13. The method of claim 12, wherein the dragging gas is an inert gas.

14. The method of claim 8, wherein the gas turbine performance test results further comprise at least one of a heat-related performance metric, a pressure-related performance metric, or a fuel-related performance metric.

15. A computer-readable storage medium having stored thereon, instructions executable by a computer for performing operations comprising:
acquiring via a transducer system, one or more functional parameters of a gas turbine;
converting via a signal converter, the acquired one or more functional parameters to gas turbine operational data;
automatically analyzing via an automated gas chromatograph, a test sample of a natural gas that is used to operate the gas turbine, wherein the automated gas chromatograph is coupled to a gas supply line of the gas turbine and is configured to automatically obtain a test sample from the gas supply line, and wherein a calibration gas container and a dragging gas container are each coupled to the automated gas chromatograph, the dragging gas to provide an inert gas for moving the test sample to the automated gas chromatograph; and transmitting the gas turbine operational data and a gas chromatography test result obtained by analyzing the test sample of the natural gas, for processing in a client computer to obtain gas turbine performance test results, wherein at least one of the gas turbine performance test results further comprise at least one of: a heat-related performance metric, a pressure-related performance metric, or a fuel-related performance metric.

16. The computer-readable storage medium of claim 15, wherein the one or more functional parameters of the gas turbine is acquired in one of a real-time mode of operation or a periodic mode of operation.

17. The computer-readable storage medium of claim 15, wherein the one or more functional parameters comprises at least one of an operating static pressure, an operating temperature, or an operating differential pressure.

18. The computer-readable storage medium of claim 15, wherein the automated gas chromatograph is coupled to a gas supply line of the gas turbine and automatically obtains a test sample of the natural gas from the gas supply line for analyzing the test sample of the natural gas.

19. The computer-readable storage medium of claim 18, having stored thereon, additional instructions executable by a computer for performing operations comprising:

calibrating the automated gas chromatograph using a calibration gas; and using a dragging gas to push through the automated gas chromatograph, the test sample of the natural gas.

20. The computer-readable storage medium of claim 19, wherein the dragging gas is an inert gas.

\* \* \* \* \*